US011166923B2

(12) United States Patent
Thummar et al.

(10) Patent No.: US 11,166,923 B2
(45) Date of Patent: *Nov. 9, 2021

(54) PARENTERAL DOSAGE FORM OF NOREPINEPHRINE

(71) Applicant: SUN PHARMACEUTICAL INDUSTRIES LIMITED, Mumbai (IN)

(72) Inventors: Rakesh Thummar, Baroda (IN); Shantaram Pawar, Baroda (IN); Prashant Kane, Baroda (IN); Subhas Balaram Bhowmick, Baroda (IN); Samarth Kumar, Baroda (IN); Milan Natvarbhai Thakkar, Baroda (IN); Kandarp Maheshkumar Dave, Baroda (IN)

(73) Assignee: SUN PHARMACEUTICAL INDUSTRIES LIMITED, Mumbai (IN)

( * ) Notice: Subject to any disclaimer, the term of this patent is extended or adjusted under 35 U.S.C. 154(b) by 0 days.

This patent is subject to a terminal disclaimer.

(21) Appl. No.: 15/875,475

(22) Filed: Jan. 19, 2018

(65) Prior Publication Data
US 2018/0140563 A1 May 24, 2018

Related U.S. Application Data

(63) Continuation of application No. 14/837,749, filed on Aug. 27, 2015, now Pat. No. 9,877,935.

(30) Foreign Application Priority Data

Aug. 28, 2014 (IN) .................... 2759/MUM/2014

(51) Int. Cl.
| A61K 31/137 | (2006.01) |
| A61K 47/10 | (2017.01) |
| A61K 31/194 | (2006.01) |
| A61K 9/00 | (2006.01) |
| A61K 9/08 | (2006.01) |
| A61K 47/22 | (2006.01) |
| A61K 31/085 | (2006.01) |
| A61K 31/00 | (2006.01) |
| A61K 31/138 | (2006.01) |
| A61K 31/191 | (2006.01) |
| A61M 5/00 | (2006.01) |

(52) U.S. Cl.
CPC .......... *A61K 31/137* (2013.01); *A61K 9/0019* (2013.01); *A61K 9/08* (2013.01); *A61K 31/00* (2013.01); *A61K 31/085* (2013.01); *A61K 31/138* (2013.01); *A61K 31/191* (2013.01); *A61K 31/194* (2013.01); *A61K 47/10* (2013.01); *A61K 47/22* (2013.01); *A61M 5/002* (2013.01); *Y02A 50/30* (2018.01)

(58) Field of Classification Search
CPC .... A61K 31/137; A61K 31/194; A61K 47/10; A61K 9/0019; A61K 9/08; A61K 31/00
See application file for complete search history.

(56) References Cited

U.S. PATENT DOCUMENTS

| 7,199,269 B2 | 4/2007 | Dinnequin |
| 7,490,639 B2 | 2/2009 | Py |
| 7,992,597 B2 | 8/2011 | Py et al. |
| 8,367,734 B1 | 2/2013 | Gao et al. |
| 2008/0208141 A1 | 8/2008 | Roth et al. |
| 2011/0003015 A1 | 1/2011 | Baillie et al. |
| 2013/0333796 A1 | 12/2013 | Py |
| 2014/0343159 A1 | 11/2014 | Fahl |
| 2017/0049720 A1 | 2/2017 | Mitidieri et al. |

FOREIGN PATENT DOCUMENTS

| AU | 2015202494 A1 | 5/2015 |
| EP | 2322541 A1 | 5/2011 |
| FR | 2779061 A1 | 12/1999 |
| JP | 2004-509920 A | 4/2004 |
| JP | 2012528830 A | 11/2012 |
| JP | 2014-515400 A | 6/2014 |
| WO | 200226223 | 4/2002 |
| WO | 2012166227 A1 | 12/2012 |

OTHER PUBLICATIONS

Duplex® Package Insert, 2009 (Year: 2009).*
F Qin et el.; "Antioxidant vitaminds prevent cardiomyocyte apoptosis produced by norephinephrine infusion in ferrets", Cardiovascular Research, vol. 51, Issue 4, pp. 736-748 (2001).
Hoellein L.; "Ficts and facts of Ephinephrine and Norophinephrine stability in injection solution", International Journal of Pharmaceutics, 434, 468-480 (2012).
Trembley M, et al.; Stability of norephinephrine infusions prepared in dextrose and normal saline solutions, Can J Anesth, 55:3, 163-167 (2008).
Walker SE, et al.; "Stability of Norephinephrine in normal saline and 5% dextrose in water", Can J Hosp Pharm, 63 (2); 113-118 (2001).
Hospira Inc.,; Material safety data sheet, 2011.; pp. 1-7.
Market, A.D. et al.; "Patenteral Nutrition-Associated Anaphylaxis in a 4-year old Child," Journal of Pediatric Gastroenterology & Nutrition; Issue; vol. 26(2), Feb. 1998, pp. 229-231.

(Continued)

Primary Examiner — Jean P Cornet
(74) Attorney, Agent, or Firm — Blank Rome LLP

(57) ABSTRACT

The present invention relates to a ready-to-administer parenteral dosage form of norepinephrine which comprises an aqueous solution of norepinephrine, having an anti-oxidant which is not a sulfite anti-oxidant, wherein the dosage form is stable at room temperature for prolonged period of time.

14 Claims, No Drawings

(56) References Cited

OTHER PUBLICATIONS

Japanese Application No. 2015-167928, Office Action dated Jun. 11, 2019, 5 pages.
Japanese Application No. 2015-167928, Office Action dated Jul. 21, 2020, 4 pages.

* cited by examiner

PARENTERAL DOSAGE FORM OF NOREPINEPHRINE

This application is a continuation of U.S. application Ser. No. 14/837,749, filed Aug. 27, 2015, which claims benefit to India Patent Application No. 2759/MUM/2014, filed on Aug. 28, 2014, in the Government of India Patent Office, the disclosure of each of which is incorporated herein by reference in its entirety.

FIELD OF THE INVENTION

The present invention relates to a ready-to-administer parenteral dosage form of norepinephrine comprising an aqueous solution of norepinephrine and an anti-oxidant which is not a sulfite anti-oxidant, and wherein the dosage form is stable at room temperature.

BACKGROUND OF THE INVENTION

Norepinephrine is a sympathomimetic amine which functions as a peripheral vasoconstrictor (alpha-adrenergic action) and as an inotropic stimulator of the heart and dilator of coronary arteries (beta-adrenergic action). It is also known as l-arterenol, levarterenol or l-norepinephrine or noradrenaline.

Norepinephrine Bitartrate, a catecholamine is chemically (−)-α-(aminomethyl)-3,4-dihydroxybenzyl alcohol tartrate (1:1) (salt) monohydrate and has the following structural formula:

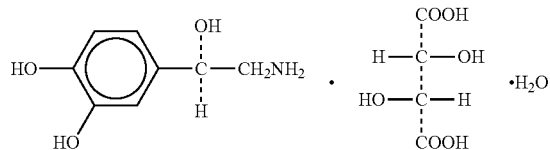

Norepinephrine (NE) is administered by intravenous infusion for blood pressure control in certain acute hypotensive states (e.g., pheochromocytomectomy, sympathectomy, poliomyelitis, spinal anesthesia, myocardial infarction, septicemia, blood transfusion, and drug reactions) and as an adjunct in the treatment of cardiac arrest and profound hypotension.

The commercial available injectable products of nor-epinephrine solutions for example, nor-epinephrine pre-concentrate solution marketed in the United States under the brand name LEVOPHED® and the solution of nor-epinephrine marketed by Cardinal Health Ltd., UK, use sodium bisulfite or sodium metabisulfite as antioxidants. A clear warning with respect to allergic reactions is included in the labels of these products, which entails cautious use of these products by the patients. The use of sulphites or sulphur is reported to cause allergic-type reactions such as anaphylactic symptoms and life-threatening or less severe asthmatic episodes in certain susceptible persons. Indeed, the symptoms of an allergic reaction to sulfites may exacerbate the condition being treated. This exacerbation is especially critical given that nor-epinephrine is often used in emergency situations where further compromising a patient with an allergic reaction is disadvantageous.

Nor-epinephrine is known to be susceptible to oxidation and degradation in presence of oxygen, particularly when present in aqueous solutions. The degradation is undesirable as it results in loss of titer of the active ingredient, formation of compounds which have undesirable physiological effects, and the appearance of a dark colour, which makes the solution offensive and unmarketable. Moreover, nor-epinephrine is known to exist in two different stereoisomeric forms: R (−) isomer and S (+) isomer, the R(−) isomer is reported to have better affinity at various receptors and thus, more potent than the S(+) isomer. The S-isomer has minimal to almost negligible activity.

The present inventors have discovered a parenteral dosage form wherein the aqueous solution of nor-epinephrine is free of sulphite antioxidant and is ready to administer. The ready-to-administer aqueous solution in the containers is not only stable at room temperature for prolonged periods of time, but also shows minimal conversion to less active S-isomer during the shelf life of the product. Further, the parenteral dosage form avoids the reconstitution or dilution step prior to intravenous infusion, thus eliminating the risk of any potential calculation or dilution error as well as risk of microbiological contamination during handling.

SUMMARY OF THE INVENTION

The present invention provides a ready-to-administer parenteral dosage form comprising an aqueous solution comprising
 a. therapeutically effective amount of norepinephrine or its pharmaceutically acceptable salt
 b. an anti-oxidant which is not a sulphite antioxidant,
wherein the solution is stable at room temperature.

DESCRIPTION OF THE INVENTION

The term norepinephrine, as used herein includes norepinephrine and/or its pharmaceutically acceptable salts such as norepinephrine bitartrate or norepinephrine hydrochloride or other salts. It is also known by other names such as l-arterenol, levarterenolol, l-norepinephrine or noradrenaline.

The term "ready-to-administer" as used herein means that the drug solution is sterile and suitable for direct intravenous infusion or injection and no intermediate steps of dilution or reconstitution are required before parenteral administration of the drug solution to the patient. The aqueous drug solution can be directly administered parenterally from the container of the dosage form. The term "ready-to-administer" is synonymous with "ready-to-infuse" or ready-to-inject" and is not to be read as the term "ready-to-use" aqueous solution. The term 'ready-to-use' in the art includes aqueous preconcentrates which require a single step of dilution with an aqueous diluent fluid such as water for injection or saline before administration. The term "ready-to-administer" is also distinguished from lyophilized products that require two steps, a first step of reconstitution to form a preconcentrate and then a second step where the preconcentrate is subjected to dilution with an aqueous infusion fluid. The ready-to-administer parenteral dosage form according to the present invention avoids the inconvenience of reconstituting or diluting a concentrated parenteral formulation into infusion diluents prior to infusion, as well as eliminates the risk of any potential calculation or dilution error as well as risk of microbiological contamination during handling. The volume of the aqueous drug solution according to the present invention is large i.e. when the end use container used in 'ready-to-administer' parenteral dosage form is a prefilled syringe, then the volume of the aqueous solution may be about 50 ml to 100 ml. When the end use container is infusion bag, the volume of the aqueous solution may be about 100 ml to 500 ml.

The term 'sulfite anti-oxidant' as used herein means any anti-oxidant capable of providing sulfite, bisulfite, or metabisulfite anions in water. For instance, sodium sulphite, sodium bisulfite, sodium metabisulphite, sodium pyrosulphite and the like.

The term 'stable at room temperature' as used herein means that the dosage form is physically as well as chemically stable as demonstrated by compliance to acceptable specification when the dosage form is stored at room temperature (about 25° C.) for twelve months, preferably eighteen months, more preferably 24 months or longer. Suitably, the solution of nor-epinephrine remains physically stable, with no precipitation or crystallization or color change upon storage and the value of percentage transmittance of the solution remaining greater than 90%, preferably greater than 95% for the shelf life period of 18-24 months when stored at room temperature. Suitably, the solution of nor-epinephrine remains chemically stable when stored at room temperature (about 25° C.) and at refrigerated conditions (2-8° C.), wherein various parameters such as the drug content (assay of nor-epinephrine) and content of related substances, i.e. known and unknown impurities remains within specified limits such as those specified according to ICH guidelines, upon storage for prolonged period of time such as for at least 12 months, preferably for 18 months, more preferably 24 months or longer. Suitably, the value of assay of nor-epinephrine remains within the specified limit of 90-110% by weight of the label claim; the highest unknown impurity remains within the specified limit of not more than 0.2%; the known Impurities B, C, D and E remains within the specified limit of not more than 0.29% and the Impurity A remains within the specified limit of not more than 1.0%. The total impurities remain below 2.0%, preferably below 1.0%.

The ready-to-administer parenteral dosage form of the present invention comprises an aqueous solution comprising therapeutically effective amount of norepinephrine or its pharmaceutically acceptable salt and an anti-oxidant which is not a sulfite anti-oxidant. Suitably, in one preferred embodiment, the pharmaceutically acceptable salt of nor-epinephrine is nor-epinephrine bitartrate. Suitably, nor-epinephrine or its pharmaceutically acceptable salt may be present in the ready-to-administer parenteral dosage form in an amount ranging from about 0.001 mg/ml to 0.4 mg/ml, preferably from about 0.002 mg/ml to 0.2 mg/ml. In one embodiment, norepinephrine is present in the aqueous solution in an amount ranging from about 0.001 mg/ml to about 0.2 mg/ml. In one embodiment, nor-epinephrine or its pharmaceutically acceptable salt is nor-epinephrine bitartrate and it is present in the aqueous solution in an amount ranging from about 0.002 mg/ml to about 0.4 mg/ml.

Suitably, the ready-to-administer parenteral dosage form of the present invention comprises an anti-oxidant which is not a sulphite anti-oxidant. Such anti-oxidants, may be selected form, but not limited to butylated hydroxyl anisol, ascorbic acid, propyl gallate, vitamin E, alpha-tocopherol, butylated hydroxyl toluene and the like. The parenteral dosage form of the present invention is devoid of sulphur containing and/or sulfite anti-oxidants such as sodium sulfite, sodium bisulfite, sodium metabisulfite or mixtures thereof. In a preferred embodiment, the anti-oxidant is butylated hydroxyanisole. Suitably, butylated hydroxyanisole is present in an amount ranging from about 0.001 mg/ml to about 0.01 mg/ml, preferably from about 0.001 mg/ml to about 0.005 mg/ml.

Suitably, the aqueous solution of the present invention may further comprise other parentally acceptable excipients, including but not limited to, osmotic/tonicity adjusting agents, chelating agents, pH adjusting agents, buffers.

Suitably, the aqueous solution according to the present invention have a pH in the range of about 3.0 to about 4.5, preferably from about 3.5 to about 4.2. The parenteral dosage form shows best stability at this pH range. The pH of the solution may be adjusted in the desired range by use of a pH adjusting agents and or a buffering agent known in the pharmaceutical art or it may be auto-adjusted in the desired range by the ingredients present in the solution of the present invention. The pH adjusting and/or buffering agent that may be used include, but are not limited to sodium hydroxide, hydrochloric acid, sulfuric acid, citric acid, acetic acid, tartaric acid, tromethamine, potassium hydroxide and the like and mixtures thereof. The aqueous solution in the parenteral dosage form of the present invention has an osmolality in the range of about 250-375 mOsm/kg, preferably 270-330 mOsm/kg. The osmolality of the aqueous solution in the dosage form of the present invention is adjusted by addition of an osmotic agent or tonicity adjusting agent. The tonicity adjusting agent that may be used according to the present invention may be selected from, but are not limited to, sodium chloride, potassium chloride, calcium chloride, mannitol, glycerol, sorbitol, propylene glycol, dextrose, sucrose, and the like and mixtures thereof. According to one preferred embodiment, the osmotic agent is sodium chloride and it may be used in an amount ranging from about 0.3% w/v to about 1.0% w/v. The aqueous solution of nor-epinephrine may further comprise a chelating agent. The chelating agent that may be used is selected form, but is not limited to, disodium edetate dihydrate, disodium edetate, edetic acid, ethylenediamine tertaacetic acid, diethylenetriamine pentaacetic acid. A preferred chelating agent is ethylenediamine tertaacetic acid or disodium edetate dehydrate.

In a preferred embodiment, the aqueous solution of nor-epinephrine according to the present invention has a dissolved oxygen level of less than 4 ppm, preferably less than 2 ppm, more preferably less than 1 ppm. This is achieved by purging the aqueous solution with an inert gas such as nitrogen or argon or helium.

The ready-to-administer parenteral dosage form of the present invention comprises a suitable container which contains the aqueous solution of norepinephrine. The container may be optionally further packaged in a secondary packaging. In one embodiment, either of the container or the secondary packaging is designed to protect the solution of nor-epinephrine from light. The secondary packaging may comprise a suitable pouch, such as an aluminium pouch and/or a carton packaging, which may further contain an oxygen scavenger. Preferably, the container is designed for ready-to-infuse or ready-to-inject the aqueous solution of norepinephrine to the patient. The container is made up of a suitable material such as plastic or any other polymeric material. The container may include one or more layers of such materials. Suitably, such materials may include but are not limited to, polyolefin polymers, polyethylene, polypropylene; cyclo olefin polymers, cyclo olefin copolymers, polypropylene based polyolefin polymers; polycarbonates; modified polyolefin-polyethylene polymers or styrene-polyolefin based polymers and block co-polymers thereof. Suitably, the container does not have material that contains borate or boron. Preferably, according to one embodiment, the container has non-glass components. Suitably, the material of construction is such that these containers are transparent which makes it possible to carry out visual inspection of the drug solution prior to and during administration of the drug solution. Any change in colour or any particulate matter can be detected easily by visual inspection, which ensures safety.

In a preferred particular embodiment of the present invention, the container is a pre-filled syringe. The pre-filled syringe is made up of a material having at least one non-glass component. The barrel of the pre-filled syringe is preferably made up of appropriate plastic or polymeric material. In a preferred aspect, the syringe comprises a barrel made up of cyclic olefin polymer, cyclic olefin copolymer, polypropylene, polycarbonate and the like. The syringe may further comprise an elastomeric tip cap, made up of material such as chloro-butyl formulation. The syringe may comprise a plunger stopper made up of rubber material such as bromo-butyl rubber. The syringe may be further packed in a secondary packaging to protect from light. The secondary packaging comprises a suitable pouch, such as an aluminium pouch and a carton packaging. The pouch may further contain an oxygen scavenger. In this embodiment, norepinephrine or its pharmaceutically acceptable salt may be present in the aqueous solution in an amount ranging from about 0.025 mg/ml to about 0.4 mg/ml, preferably from about 0.05 mg/ml to about 0.2 mg/ml. In one particularly preferred embodiment, norepinephrine or its pharmaceutically acceptable salt is nor-epinephrine bitartrate and it is present in the aqueous solution in an amount of 0.2 mg/ml which is approximately equivalent to 0.1 mg/ml of norepinephrine base. In this embodiment, the volume of the aqueous solution in pre-filled syringe may vary from about 50 ml to about 100 ml. According to preferred embodiment, the ready-to-administer parenteral dosage form provides large volume pre-filled syringes, which can accommodate a volume of at least 50 ml, preferably about 50 ml to 100 ml.

In another preferred embodiment of the present invention, the container is an infusion bag. In this embodiment, norepinephrine or its pharmaceutically acceptable salt is present in the aqueous solution in an amount ranging from about 0.001 mg/ml to about 0.2 mg/ml, preferably from about 0.004 mg/ml to about 0.15 mg/ml, more preferably from about 0.01 mg/ml to about 0.1 mg/ml. In one preferred embodiment, norepinephrine is present in the aqueous solution in an amount of 0.016 mg/ml. In one preferred embodiment, norepinephrine is present in the aqueous solution in an amount of 0.032 mg/ml. The volume of aqueous solution in each bag may vary from about 100 ml to about 500 ml. According to preferred embodiments of the present invention, the ready-to-administer parenteral dosage form provides large volume infusion bags, which can accommodate a volume of at least 100 ml, preferably from about 100 ml to 500 ml. The aqueous solution comprises the nor-epinephrine at a concentration which allows direct infusion of the aqueous solution in the desired dose to the patient without the need of further dilution. The containers have volume and dimensions such that it allows use of drug solutions that can be directly infused to the patients without any step of reconstitution or dilution. Preferably, the concentration and volume is such that for patient with an average body surface area, only one unit of the dosage form is sufficient to deliver the prescribed dose of the drug. The containers are also easy to handle and transport.

According to another preferred particular embodiment of the present invention, the aqueous solution of norepinephrine is ready-to-infuse and container is designed for ready-to-infuse administration. In one preferred embodiment, the container is a flexible infusion container such an infusion bag or a flexible pouch or a soft bag. Particularly, the flexible infusion container is not impermeable in nature and possesses some permeation characteristics and the aqueous solution of nor-epinephrine remains in contact with these materials of the container throughout the shelf life of the dosage form. The container may be single or multiple layered and made up of a suitable material such as plastic or any other polymeric material. Such materials may be selected from, but not limited to, polyolefin polymers-polyethylene, polypropylene; cyclo olefin polymers, cyclo olefin copolymers, polypropylene based polyolefin polymers; modified polyolefin-polyethylene polymers or styrene-polyolefin based polymers and block co-polymers thereof. These plastic materials of the container may further have one or more outer layers which may be made up of polyamide, modified polyolefin, polypropylene, styrene-polyolefin based polymers and block co-polymers thereof and the like. In one specific embodiment, the flexible infusion containers are made up of an outer layer of polyamide 11, a middle tie of modified polyolefin and an inner layer of linear low density polyethylene. This type of containers have a water vapour transmission rate of 2 g $(m^2 \cdot day)$ when measured at (40° C./90% relative humidity); oxygen transmission rate of 900 ml/$(m^2 \cdot 24$ hour·atm) when measured at (23° C./0% relative humidity) and carbon dioxide transmission rate of 600 ml/$(m^2 \cdot 24$ hour·atm) when measured at 23° C./0% relative humidity. Such containers are available commercially and are manufactured by Hosokawa as Polyelite AE-1.

In one preferred embodiment the flexible infusion containers may be made up of a material comprising a polymer of cyclic olefin such as cycloolefin homopolymer or cycloolefin copolymer or mixture thereof. Specifically, in a particular embodiment, the container comprises an inner layer made up of a cycloolefin polymer, a middle layer made up of linear low density polyethylene polymer and an outer layer made up of low density polyethylene polymer. Such containers are available commercially and are manufactured by Hosokawa as Polyelite EHC film bag. In another embodiment, the flexible infusion containers may be made up of an outer layer of polypropylene polymer with styrene-ethylene-butylene (SEB) block copolymer and a middle and inner layer made up of polypropylene based polyolefin polymer with styrene-ethylene butylene block copolymer. Such containers are available commercially and are manufactured by Technoflex These type of containers have a water vapour transmission rate of 0.62 g $(m^2 \cdot day)$ when measured at 23° C./60% relative humidity; oxygen permeability of 1110 ml/$(m^2 \cdot 24$ hour·atm) when measured at 23° C./40% relative humidity and carbon dioxide transmission rate of 5149 ml/$(m^2 \cdot 24$ hour·atm). Alternatively, the flexible container used is made up of multilayer polyolefin film (M312 and M312A) with a multilayered polyolefin tubing (M916 and M916A). Such containers are available under the brand names of Sippex.

In one embodiment, the flexible infusion containers may include a Minitulipe® infusion port which is an infusion connector having three assembled parts including a central stopper made up of chlorobutyl rubber (latex free); an upper breakable part and a bottom part, both made up of polycarbonate. In one embodiment, the flexible infusion container contains a delivery port end for insertion of an infusion set cannula/needle. In one embodiment, the flexible infusion container/bag and the delivery port connecting to the infusion needle form a system whereby during administration of the solution to the patient the vacuum created by outgress of solution is accommodated by the elasticity or flexibility of the infusion bag instead of ingress of external non-sterile air.

The dosage form can advantageously maintain the sterility of the solution until it reaches the patient.

In one embodiment, the flexible infusion container includes a thermally resealable portion that is fusible in response to thermal energy, and a container body having a sealed empty chamber in fluid communication with the resealable portion for receiving therein the aqueous solution of the present invention. The method of filling the container includes penetrating the resealable portion with an injection member and introducing the aqueous solution of the present invention into the chamber, withdrawing the injection member while engaging the base of the body to substantially prevent axial movement of the body, and applying thermal energy to the resealable portion to thermally fuse the penetrated region thereof. Such systems are elaborated in Unites States patent number U.S. Pat. No. 7,992,597, which is incorporated herein by reference.

In another embodiment, the flexible infusion container may include a chamber for receiving aqueous solution of the present invention and a thermoplastic portion in fluid communication with the chamber. The thermoplastic portion defines a penetrable region that is penetrable by a filling member and is heat resealable to hermetically seal an aperture therein by applying laser radiation at a predetermined wavelength and power and in a predetermined time period. Such systems are elaborated in Unites States patent number U.S. Pat. No. 7,490,639, which is incorporated herein by reference.

In yet another embodiment, the flexible infusion container include a sealed chamber; a first penetrable septum in fluid communication with the chamber that is formed of an elastic material and is penetrable by a first injection member to fill the first chamber with the aqueous solution of the present invention therethrough; and a second penetrable septum movable between first and second positions. In the first position, at least a portion of the second septum is spaced away from the first septum to allow the injection member to penetrate the first septum and aseptically or sterile fill the chamber with the aqueous solution of the present invention therethrough. In the second position, the portion of the second septum overlies and seals a resulting injection aperture in the first septum after withdrawal of the first injection member therefrom, and is penetrable by a second injection member to penetrate the first and second septums and withdraw the filled aqueous solution of the present invention from the chamber and through the second injection member. Such systems are elaborated in Unites States patent application number US20130333796, which is incorporated herein by reference.

In one embodiment, the ready-to-administer dosage form of the present invention further comprises secondary packaging that surrounds the flexible infusion container. In one embodiment, the secondary packaging is designed to protect the solution from light. The secondary packaging may comprise a second container such as a pouch or overwrap or carton. In preferred embodiments, the secondary packaging pouch or overwrap or carton is made up of a suitable light protective material such as aluminum. It may further comprise an oxygen scavenger. In one preferred embodiment, the space between the flexible infusion container and secondary packaging is occupied with an inert gas. The inert gas may be used to flush out or replace the air from the space between the flexible infusion container and the light protective secondary packaging. The inert gas that may be used include, but is not limited to nitrogen, argon and helium. In one specific embodiment, secondary packaging comprises an aluminium pouch containing an oxygen scavenger. In another embodiment, the space between the flexible infusion container and secondary packaging is occupied with an inert gas such as nitrogen.

In one specific embodiment, there is provided a ready-to-administer parenteral dosage form comprising an aqueous solution comprising therapeutically effective amount of norepinephrine or its pharmaceutically acceptable salt, an antioxidant which is not a sulphite antioxidant selected from butylated hydroxyl anisol, ascorbic acid, propyl gallate, vitamin E or alpha-tocopherol, optionally a chelating agent, a tonicity adjusting agent and a pH adjusting agent to adjust the pH of solution in the range of 3.0 to 4.5 and wherein the aqueous solution is stable at room temperature.

In another specific embodiment, there is provided a ready-to-administer parenteral dosage form comprising an aqueous solution comprising therapeutically effective amount of norepinephrine or its pharmaceutically acceptable salt, butylated hydroxyl anisol as an antioxidant, optionally a chelating agent, a tonicity adjusting agent and a pH adjusting agent to adjust the pH of solution in the range of 3.0 to 4.5 and wherein the aqueous solution is stable at room temperature.

In one specific embodiment, there is provided a ready-to-administer parenteral dosage form comprising an aqueous solution comprising therapeutically effective amount of norepinephrine or its pharmaceutically acceptable salt in an amount ranging from about 0.001 mg/ml to about 0.4 mg/ml, an antioxidant which is not a sulphite antioxidant, optionally a chelating agent, a tonicity adjusting agent and a pH adjusting agent to adjust the pH of solution in a range of 3.0 to 4.5, wherein the aqueous solution is filled in a container, which container is optionally further packaged in a secondary packaging, wherein either the container or the secondary packaging is designed to protect the solution from light and wherein the aqueous solution is stable at room temperature.

In one specific embodiment, there is provided a ready-to-administer parenteral dosage form comprising an aqueous solution comprising therapeutically effective amount of norepinephrine or its pharmaceutically acceptable salt in an amount ranging from about 0.001 mg/ml to about 0.4 mg/ml, an antioxidant which is not a sulphite antioxidant, optionally a chelating agent, a tonicity adjusting agent and a pH adjusting agent to adjust the pH of solution in a range of 3.0 to 4.5, wherein the aqueous solution is filled in a container, which container is optionally further packaged in a secondary packaging, wherein either the container or the secondary packaging is designed to protect the solution from light, further wherein the container is made up of a material selected from the group comprising polyolefin polymers, polyethylene, polypropylene; cyclo olefin polymers, cyclo olefin copolymers; polypropylene based polyolefin polymers; polycarbonates; modified polyolefin-polyethylene polymers; styrene-polyolefin based polymers and block co-polymers thereof and wherein the aqueous solution is stable at room temperature. In one preferred embodiment, there is provided a ready-to-administer parenteral dosage form comprising an aqueous solution comprising therapeutically effective amount of norepinephrine bitartrate in an amount ranging from about 0.002 mg/ml to about 0.4 mg/ml, butylated hydroxyanisole as an antioxidant, a chelating agent, a tonicity adjusting agent and a pH adjusting agent to adjust the pH of solution in a range of 3.0 to 4.5, wherein the aqueous solution is filled in a container, which container is optionally further packaged in a secondary packaging, wherein either the container or the secondary packaging is designed to protect the solution from light and wherein the aqueous solution is stable at room temperature.

In another preferred embodiment, there is provided a ready-to-administer parenteral dosage form comprising an aqueous solution comprising therapeutically effective amount of norepinephrine bitartrate in an amount ranging from about 0.002 mg/ml to about 0.4 mg/ml, butylated hydroxyanisole as an antioxidant, a chelating agent, a tonicity adjusting agent and a pH adjusting agent to adjust the pH of solution in a range of 3.0 to 4.5, wherein the aqueous solution is filled in a container, which container is optionally further packaged in a secondary packaging, wherein either the container or the secondary packaging is designed to protect the solution from light, further wherein the container is made up of a material selected from the group comprising polyolefin polymers, polyethylene, polypropylene; cyclo olefin polymers, cyclo olefin copolymers; polypropylene based polyolefin polymers; polycarbonates; modified polyolefin-polyethylene polymers; styrene-polyolefin based polymers and block co-polymers thereof, and wherein the aqueous solution is stable at room temperature.

In one particularly preferred embodiment, there is provided a ready-to-administer parenteral dosage form comprising an aqueous solution comprising therapeutically effective amount of norepinephrine bitartrate in an amount ranging from about 0.002 mg/ml to about 0.4 mg/ml, butylated hydroxyanisole as an antioxidant, a chelating agent selected from disodium edetate, disodium edetate dihydrate, edetic acid, ethylenediamine tertaacetic acid or diethylenetriamine pentaacetic acid, a tonicity adjusting agent selected from sodium chloride, potassium chloride, calcium chloride, mannitol, glycerol, sorbitol, propylene glycol, dextrose, sucrose and a pH adjusting agent to adjust the pH of solution in a range of 3.0 to 4.5, wherein the aqueous solution is filled in a container, which container is optionally further packaged in a secondary packaging, wherein either the container or the secondary packaging is designed to protect the solution from light and wherein the aqueous solution is stable at room temperature.

In one particularly preferred embodiment, there is provided a ready-to-administer parenteral dosage form comprising an aqueous solution comprising therapeutically effective amount of norepinephrine bitartrate in an amount ranging from about 0.002 mg/ml to about 0.4 mg/ml, butylated hydroxyanisole as an antioxidant, a chelating agent selected from disodium edetate, disodium edetate dihydrate, edetic acid, ethylenediamine tertaacetic acid or diethylenetriamine pentaacetic acid, a tonicity adjusting agent selected from sodium chloride, potassium chloride, calcium chloride, mannitol, glycerol, sorbitol, propylene glycol, dextrose, sucrose and a pH adjusting agent to adjust the pH of solution in a range of 3.0 to 4.5, wherein the aqueous solution is filled in a container, which container is optionally further packaged in a secondary packaging, wherein either the container or the secondary packaging is designed to protect the solution from light further wherein the container is made up of a material selected from the group comprising polyolefin polymers, polyethylene, polypropylene; cyclo olefin polymers, cyclo olefin copolymers; polypropylene based polyolefin polymers; polycarbonates; modified polyolefin-polyethylene polymers; styrene-polyolefin based polymers and block co-polymers thereof, and wherein the aqueous solution is stable at room temperature.

In one particularly preferred embodiment, there is provided a ready-to-administer parenteral dosage form comprising an aqueous solution comprising therapeutically effective amount of norepinephrine bitartrate in an amount ranging from about 0.01 mg/ml to about 0.2 mg/ml, butylated hydroxyanisole as an antioxidant, a chelating agent selected from disodium edetate dihydrate, disodium edetate, edetic acid, ethylenediamine tertaacetic acid or diethylenetriamine pentaacetic acid, a tonicity adjusting agent selected from sodium chloride, potassium chloride, calcium chloride, mannitol, glycerol, sorbitol, propylene glycol, dextrose, sucrose and a pH adjusting agent to adjust the pH of solution in a range of 3.0 to 4.5, wherein the aqueous solution is filled in a container, which container is optionally further packaged in a secondary packaging, wherein either the container or the secondary packaging is designed to protect the solution from light further wherein the container is made up of a material selected from the group comprising polyolefin polymers, polyethylene, polypropylene; cyclo olefin polymers, cyclo olefin copolymers; polypropylene based polyolefin polymers; polycarbonates; modified polyolefin-polyethylene polymers; styrene-polyolefin based polymers and block co-polymers thereof, further wherein the secondary packaging comprises a light resistant pouch such as an aluminium pouch and an oxygen scavanger and wherein the aqueous solution is stable at room temperature.

The present inventors have surprisingly found that the ready-to-administer parenteral dosage form of the present invention is stable at room temperature for prolonged period of time inspite of having large volume aqueous solution in large volume infusion containers. The aqueous solution of norepinephrine is stable at room temperature for extended periods of time in the liquid state, without having to undergo a step of freeze-drying or reconstitution or dilution. That is it represents a substantial advancement over the art, and a major convenience to potential patients.

The ready-to-administer parenteral dosage form of the present invention is physically and chemically stable at room temperature (about 20-25° C.) as well as at lower temperatures such as 2-8° C. for prolonged period of time, and meets all acceptable stability criteria's upon storage for prolonged periods such as for at least 18 months, preferably 2 year or more. The solution remains physically stable, with no precipitation or crystallization or color change upon storage. The percentage transmittance values, which are indicators of clarity and physical stability of a solution, surprisingly remains greater than 90%, preferably greater than 95%, more preferably greater than 97% for the shelf life period of 18-24 months.

The ready-to-administer parenteral dosage form of the present invention comprising the aqueous solution of nor-epinephrine also remains chemically stable when subjected to long term stability testing at room temperature (25° C./60% relative humidity) and at refrigerated conditions (2-8° C.). Various parameters such as the drug content (assay of nor-epinephrine) and content of related substances, i.e. known and unknown impurities remains within specified limits such as those specified according to ICH guidelines, upon storage for prolonged period of time such as for at least 12 months, preferably for 18 months, more preferably 2 year or more. Suitably, the value of assay of nor-epinephrine remains within the specified limit of 90-110% of the label claim. Further, the total impurities remains below 2.0%, preferably less than 1.0% more preferably less than 0.5% by weight and highest unknown impurity remains below 0.2%. Furthermore, the known related substances, i.e. Impurities B, C, D and E remains within the specified limit of not more than 0.29% and Impurity A remains within the specified limit of not more than 1.0%.

In one preferred embodiment, the present invention thus provides a ready-to-administer parenteral dosage form comprising an aqueous solution comprising therapeutically effective amount of norepinephrine or its pharmaceutically acceptable salt, an anti-oxidant which is not a sulphite antioxidant, wherein the parenteral dosage form is stable at room temperature and wherein the value of total impurities in the aqueous solution is not more than 2.0% by weight upon storage at room temperature or lower for at least 12 months.

Surprisingly, the inventors of the present invention found that the ready-to-administer parenteral dosage form of the present invention provided a very minimal conversion of the nor-epinephrine R-isomer, which is the active form, into the S-isomer. This is particularly of great significance because S-isomer has almost negligible activity. The S-isomer levels remains very low, preferably less than 5%, more preferably less than 4% upon storage at room temperature or lower temperatures for at least 12 months or 18 months or more. The conversion of R-isomer to S-isomer was significantly lower compared to the marketed product Levophed® upon storage under similar conditions. Upon storage of Innovator's US marketed product "Levophed® under similar conditions and analysing at the end of shelf life (18 months), the S-isomer level was about 6.7%. Upon storage of Innovator's European marketed product "Levophed® under similar conditions, the S-isomer level was about 15.9% after storage for 18 months. In contrast, the present invention provides a ready-to-administer parenteral dosage form comprising an aqueous solution comprising therapeutically effective amount of norepinephrine or its pharmaceutically acceptable salt and an anti-oxidant which is not a sulphite antioxidant and wherein the solution when stored at room temperature or lower for 12 months has less than 4% of S-isomer content, preferably less than 4% of S-isomer content. According to one preferred embodiment of the present invention wherein the dosage form is a pre-filled syringe, and wherein the aqueous solution has a pH in the range of about 3.0 to 4.5, the S-isomer content was about 1.7% upon storage at room temperature or lower for 12 months. According to another preferred embodiment of the present invention wherein the dosage form is in a flexible infusion bag, the S-isomer level was about 4.5% upon storage at room temperature or lower for 18 months. In one preferred embodiment, the present invention thus provides a ready-to-administer parenteral dosage form comprising an aqueous solution comprising therapeutically effective amount of norepinephrine or its pharmaceutically acceptable salt, an anti-oxidant which is not a sulphite antioxidant, wherein the solution when stored at room temperature for twelve months has less than 4% of S-isomer content.

The ready-to-administer parenteral dosage form of norepinephrine of the present invention, show improved stability, in particular stability against auto-oxidation and thermal stability, and consequently enhanced storage shelf-life of at least 18 months, preferably 2 year or more, even when stored at room temperature. A prior known solution of nor-epinephrine marketed by Cardinal Health Ltd., UK, which is stabilized by sodium metabisulphite, is stable when stored at 2-8° C. for six months. The shelf life of the product is only six months when stored at 2-8° C. Present inventors prepared similar dosage form and stability testing at room temperature confirmed that norepinephrine was unstable in the prior known sodium metabisulphite containing dosage form when stored at room temperature. While the shelf life of marketed Cardinal's product is 6 months, when stored at 2-8° C., the parenteral dosage form according to one embodiment of the present invention was surprisingly found to be stable even at room temperature (25° C./60% RH) (besides being stable at 2-8° C.) for prolonged period of time of at least 12 months, preferably 18 months, more preferably 2 year or more. The ready-to-administer parenteral dosage form of the present invention not only have better stability profile compared to marketed Cardinal's product, but also compared to marketed Levophed® product, which is a concentrated product having 1 mg/ml nor-epinephrine. As per Levophed® product label, the product upon dilution is stable only upto 24 hours at room temperature.

Suitably, the ready-to-administer dosage form of the present invention is sterile. The term "sterile" or 'sterilized' as used in the context of the invention, means that the solution has been brought to a state of sterility and has not been subsequently exposed to microbiological contamination, i.e. the sterility of the solution present in the container has not been compromised. The solution complies with the sterility requirements of the standard Pharmacopoeias like United States Pharmacopoeias (USP). Sterilization may be achieved by suitable techniques such as filtration sterilization, radiation sterilization and the like. In one preferred embodiment, the parenteral dosage form of the present invention is subjected to sterilization by membrane filtration of the aqueous solution.

The ready-to-administer parenteral dosage form of the present invention can be prepared by a process involving following exemplary steps—Purging water for injection with Nitrogen gas to bring dissolved oxygen level below 2 PPM, preferably below 1 PPM. Preferably, the purging should be carried out during the whole process to maintain dissolved oxygen level of less than 1 PPM. Dissolving the chelating agent such as disodium edetate dihydrate in water for injection followed by addition and dissolution of anti-oxidant such as butylated hydroxyanisole. Dissolution may be carried out by warming the solution to an elevated temperature, if required along with stirring. Cooling the solution to room temperature. Adding and dissolving an osmotic agent such as for example, sodium chloride to the above solution. Adding the drug, norepinephrine bitartarate, to the above solution and obtaining final solution by making up the volume to desired level using water for injection. Checking and if required adjusting the pH of the solution in the range of pH 3.0 to 4.5 using a pH adjusting agent and/or buffering agent such as by using buffers or use of an acid/base. Aseptically filtering the solution using a membrane filter, followed by aseptically filling the solution into a container such as for example a syringe or an infusion bag, followed by stoppering or sealing of the container. Optionally, packaging this primary container further with a secondary packaging. This may be achieved by overwrapping the primary container by a light protective secondary packaging such as an aluminum pouch and sealing the pouch. An oxygen scavenger may be placed in the space between the primary container and the light protective secondary packaging. Further, the space between the infusion bag and the aluminum pouch may be replaced with an inert gas such as nitrogen gas.

Hereinafter, the invention will be more specifically described by way of Examples. The examples are not intended to limit the scope of the invention and are merely used as illustrations.

Example 1

TABLE 1

Ready-to-administer parenteral dosage form composition

| Ingredients | Amount in milligrams |
|---|---|
| Norepinephrine bitartarate equivalent to norepinephrine base . . . | 5 |
| Butylated hydroxyanisole | 0.15 |
| Disodium edetate dihydrate | 5 |
| Sodium chloride | 450 |
| Sodium hydroxide/hydrochloride acid | q.s. to pH 3.0 to 4.5 |
| Water for injection | q.s. to 50 ml |

The water for injection was purged with nitrogen until dissolved oxygen level below 1.0 ppm is achieved. Aqueous solution of disodium edetate, sodium chloride was prepared separately. Butylated hydroxyanisole was dissolved in warm water. Subsequently, norepinephrine bitartarate was then added and pH was adjusted in the range of 3.0 to 4.5 using acid/base and volume was made. The oxygen level was monitored to be below 1.0 ppm by nitrogen purging. The solution so obtained was filtered aseptically through a 0.2 micron membrane filter and aseptically filled into non glass container which is a cyclo olefin copolymers syringe with fill volume of 50 ml. The filled syringe was aseptically stoppered with a bromo-butyl plunger. The filled syringes were overwrapped in aluminum pouch, for light protection. The space between the filled syringe and the aluminum pouch was replaced with nitrogen gas. An oxygen scavenger was placed in the space between the syringe and the aluminum pouch.

The observed values for various parameters after storage for 18 month at controlled room temperature of 25±2° C. and 60%±5% relative humidity, are given below in Table 2:

TABLE 2

Observations of various parameters

| Parameters | Initial | 12 month |
|---|---|---|
| Assay of nor-epinephrine | 105.11 | 105.4 |
| S-isomer | 0.18 | 4.49 |
| Impurity A | ND | ND |
| Impurity B | 0.005 | 0.024 |
| Impurity C | ND | ND |
| Impurity D | 0.06 | 0.06 |
| Impurity E | ND | ND |
| Highest unknown Impurity | 0.06 | 0.11 |
| Total Impurities | 0.12 | 0.39 |
| pH | 3.7 | 3.73 |
| % Transmittance at 650 nm | 99.96 | 99.8 |

ND—Not detected

It was found that upon storage for 18 months at room temperature, the solutions remained clear and colourless, without any signs of precipitation or crystallization or colour change upon storage. This is evident by the percentage transmittance values which were more than 95% at all time points until 18 months. The observed percentage transmittance value after storage for 18 months was found to be more than 95%. It was further observed that the value of assay of nor-epinephrine was well within the specified limit of 90-110% of the label claim. Further, the solution had less than 0.5% of total impurities and less than 0.2% of highest unknown impurity upon storage at room temperature for 18 months. The S-isomer content was less than 5%. The Impurities A-E were either not detected or were present in negligible amounts, well within the specified limits.

Example 2

TABLE 3

Aqueous solution of Norepinephrine in infusion bag

| Ingredients | Amount in milligrams per ml |
|---|---|
| Norepinephrine bitartarate equivalent to norepinephrine base . . . | 0.016 |
| Butylated Hydroxyanisole | 0.003 |
| Disodium Edetate Dihydrate | 0.1 |
| Sodium chloride | 8.5 |
| Sodium hydroxide/hydrochloride acid | q.s. to pH 3.0 to 4.5 |
| Water for Injection | q.s. to 1 mL |

The water for injection was purged with nitrogen until dissolved oxygen level below 1.0 ppm is achieved. Aqueous solution of disodium edetate, sodium chloride was prepared separately. Butylated hydroxyanisole was dissolved in warm water. Subsequently, norepinephrine bitartarate was then added and pH was adjusted in the range of 3.0 to 4.5 using acid/base and volume was made. The oxygen level was monitored to be below 1.0 ppm by nitrogen purging. The solution so obtained was filtered aseptically through a 0.2 micron membrane filter and aseptically filled into a suitable infusion container made up of polyethylene polymer in volumes of 100 ml each. The filled infusion bags were overwrapped in aluminum pouch, for light protection. The space between the infusion bag and the aluminum pouch was replaced with nitrogen gas. An oxygen scavenger was placed in the space between the infusion bag and the aluminum pouch.

The ready-to-administer dosage form of nor-epinephrine was subjected to accelerated stability conditions, such as at controlled room temperature, i.e. 25° C./40% relative humidity and at 2-8° C. The drug content and related substances, i.e. known and unknown impurities were analyzed. The details are given below in Table 4:

TABLE 4

Results of the stability testing

| Parameters | Initial | Stored at 25 ± 2° C. and 60% ± 5% relative humidity for 12 month |
|---|---|---|
| Assay | 101 | 100 |
| S-isomer | 0.31 | 1.7 |
| Impurity A | ND | ND |
| Highest unknown Impurity | 0.04 | 0.14 |
| Total impurities | 0.1 | 0.27 |
| pH | 4.2 | 4.2 |
| % Transmittance at 650 nm | 99.9 | 99.8 |

ND—Not detected

It was observed that the value of assay of nor-epinephrine was well within the specified limit of 90-110% of the label claim. Further, the solution showed a very small increase in the impurities such as known and unknown. The highest unknown impurity was very low i.e 0.2%. The aqueous solution did not show any signs of precipitation or crystallization or discoloration. The s-isomer content, which is an inactive isomer, was unexpectedly found to be very low, much lower than 2%.

The invention claimed is:

1. An aqueous solution comprising norepinephrine or its pharmaceutical acceptable salt, an antioxidant comprising butylated hydroxyl anisole in an amount ranging from about 0.001 mg/ml to about 0.01 mg/ml, wherein said aqueous solution is stable at room temperature for at least 12 months.

2. The aqueous solution according to claim 1, wherein said aqueous solution is in a container and is a ready-to-infuse solution.

3. The aqueous solution according to claim 1, wherein the norepinephrine or its pharmaceutically acceptable salt is norepinephrine bitartrate.

4. The aqueous solution according to claim 3, wherein the norepinephrine bitartrate is present in an amount ranging from about 0.001 mg/ml to about 0.4 mg/ml.

5. The aqueous solution according to claim 1, wherein said solution further comprises an antioxidant, which is not a sulphite antioxidant, selected from the group consisting of butylated hydroxyl toluene, ascorbic acid, propyl gallate, vitamin E and alpha-tocopherol.

6. The aqueous solution according to claim 1, wherein the pH of the aqueous solution is in the range of about 3.0 to about 4.5.

7. The aqueous solution according to claim 2, wherein the aqueous solution in the container is further packaged in a secondary packing, wherein either the container or secondary packing is designed to protect the solution of norepinephrine from light.

8. The aqueous solution according to claim 7, wherein the container comprises material selected from the group consisting of polyolefin polymers, polyethylene, polypropylene, cyclo-olefin polymers, cyclo-olefin copolymers, polypropylene based polyolefin polymers, polycarbonates, modified polyolefin-polyethylene polymers, and styrene-polyolefin based polymers and block co-polymers thereof.

9. The aqueous solution according to claim 7, wherein the secondary packing comprises an aluminum pouch and an oxygen scavenger.

10. The aqueous solution according to claim 1, wherein the aqueous solution when stored at room temperature for 12 months has less than 4% of S-isomer content.

11. The aqueous solution according to claim 1, wherein the aqueous solution has total impurities not more than 2.0% by weight after storage at room temperature for at least 12 months.

12. A stable parenteral dosage form comprising a ready-to-infuse aqueous solution of from about 0.001 mg/ml to about 0.4 mg/ml norepinephrine, or its pharmaceutical acceptable salt, and butylated hydroxyl anisole in an amount up to about 0.01 mg/ml, said aqueous solution having an osmolality in the range of about 250-375 mOsm/kg, and wherein the solution is stable at room temperature for at least 12 months.

13. A stable parenteral dosage form comprising an aqueous solution of from about 0.001 mg/ml to about 0.4 mg/ml norepinephrine, or its pharmaceutical acceptable salt, and butylated hydroxyl anisole in an amount up to about 0.01 mg/ml, wherein said solution has more than 95% transmittance values and less than 0.5% of highest unknown impurity upon storage at room temperature for at least 12 months.

14. A ready-to-administer parenteral dosage form comprising a solution of from about 0.001 mg/ml to about 0.4 mg/ml norepinephrine bitartrate, butylated hydroxyl anisole in an amount up to about 0.01 mg/ml, a chelating agent, and an osmogen in an infusion container, wherein the pH of the aqueous solution is 3.0 to 4.5 and a dissolved oxygen level below 2 ppm, and wherein the solution is stable at room temperature for at least 12 months.

* * * * *